(12) United States Patent
Abuzeni

(10) Patent No.: US 12,068,064 B2
(45) Date of Patent: Aug. 20, 2024

(54) PRESCRIPTION DATA VERIFICATION

(71) Applicant: XEOTECH, LLC, Jacksonville, FL (US)

(72) Inventor: Patrick Abuzeni, Jacksonville, FL (US)

(*) Notice: Subject to any disclaimer, the term of this patent is extended or adjusted under 35 U.S.C. 154(b) by 262 days.

(21) Appl. No.: 16/882,649

(22) Filed: May 25, 2020

(65) Prior Publication Data

US 2020/0286607 A1 Sep. 10, 2020

Related U.S. Application Data

(63) Continuation-in-part of application No. 14/289,219, filed on May 28, 2014, now Pat. No. 10,665,336.

(51) Int. Cl.
| | |
|---|---|
| G16H 20/10 | (2018.01) |
| G06F 21/60 | (2013.01) |
| G06K 19/06 | (2006.01) |
| G16H 10/60 | (2018.01) |
| H04L 9/40 | (2022.01) |

(52) U.S. Cl.
CPC ............ *G16H 20/10* (2018.01); *G06F 21/602* (2013.01); *G06K 19/06037* (2013.01); *G16H 10/60* (2018.01); *H04L 63/0428* (2013.01)

(58) Field of Classification Search
CPC ...... G16H 20/10; G16H 10/60; G06F 21/602; H04L 63/0428
See application file for complete search history.

(56) References Cited

U.S. PATENT DOCUMENTS

| | | | |
|---|---|---|---|
| 2004/0068690 A1* | 4/2004 | Wood ..................... | G16H 10/20 715/205 |
| 2006/0259330 A1* | 11/2006 | Schranz ................. | G06Q 10/10 235/487 |
| 2006/0261145 A1* | 11/2006 | Robertson .............. | G16H 20/10 235/375 |
| 2007/0083494 A1* | 4/2007 | Carlson .................. | G06Q 10/10 |
| 2007/0232885 A1* | 10/2007 | Cook ..................... | G16H 30/40 600/407 |
| 2008/0201173 A1* | 8/2008 | Takehara ................ | G16H 20/10 705/3 |
| 2009/0013385 A1* | 1/2009 | Olczak ................... | H04L 9/32 726/4 |
| 2009/0112882 A1* | 4/2009 | Maresh ................... | G16H 30/20 |
| 2009/0157424 A1* | 6/2009 | Hans ..................... | G06Q 10/107 705/2 |
| 2010/0268550 A1* | 10/2010 | Abuzeni ................. | G16H 20/10 705/2 |

(Continued)

*Primary Examiner* — Mark Holcomb

(57) ABSTRACT

A method and system for requesting and receiving prescription verification is described. A patient may establish a secure communication with a cloud-based server and receive a machine-readable code including the patient's encrypted information. The patient may present the code to a physician, whereupon the physician may communicate the coded patient information to the cloud-based server and the physician may communicate prescription information to an electronic clearinghouse. Upon patient's presentation of the code to a pharmacy, the pharmacist may verify the prescription with the clearinghouse; the clearinghouse validating the patient information with the cloud-based server. Upon verification, the pharmacist may fill the prescription.

8 Claims, 8 Drawing Sheets

(56) References Cited

U.S. PATENT DOCUMENTS

| | | | | |
|---|---|---|---|---|
| 2012/0203078 A1* | 8/2012 | Sze | ........................ | G16H 40/67 |
| | | | | 600/301 |
| 2013/0317835 A1* | 11/2013 | Mathew | ................ | G06Q 10/10 |
| | | | | 705/40 |
| 2014/0136235 A1* | 5/2014 | Lee | ........................ | G16H 10/60 |
| | | | | 705/3 |
| 2014/0279807 A1* | 9/2014 | Dimitrijevic | .......... | G16H 50/20 |
| | | | | 706/47 |
| 2018/0285524 A1* | 10/2018 | Ishikawa | ................ | G16H 30/20 |

* cited by examiner

PRESCRIPTION DATA VERIFICATION

CLAIM OF PRIORITY

This application claims the benefit of priority under 35 USC § 120 as a continuation-in-part of U.S. Non-Provisional patent application Ser. No. 14/289,219, filed on May 28, 2014, and entitled "Prescription Price Messenger", which is incorporated herein by reference as if set forth herein in its entirety.

COPYRIGHT AND TRADEMARK NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever. Trademarks are the property of their respective owners.

BACKGROUND

Currently, prescription medication is given to a patient by a doctor through the use of the ubiquitous prescription pad and prescription pricing may only be revealed when the prescription is presented for fulfillment at a pharmacy. Prescriptions are written by the doctor and given to a patient to get filled at the nearest pharmacy. Systems that wish to provide a little more security may use a client/server-based application to write a prescription and have the client application send the prescription to a secure server located at a pharmacy or other medication dispensation facility. In either case, a prescription is provided to a patient that contains patient information as well as medication and dosage information such that the patient may utilize a favored medication dispensation facility.

BRIEF DESCRIPTION OF THE DRAWINGS

Certain illustrative embodiments illustrating organization and method of operation, together with objects and advantages may be best understood by reference detailed description that follows taken in conjunction with the accompanying drawings in which.

DETAILED DESCRIPTION

Figure 1:
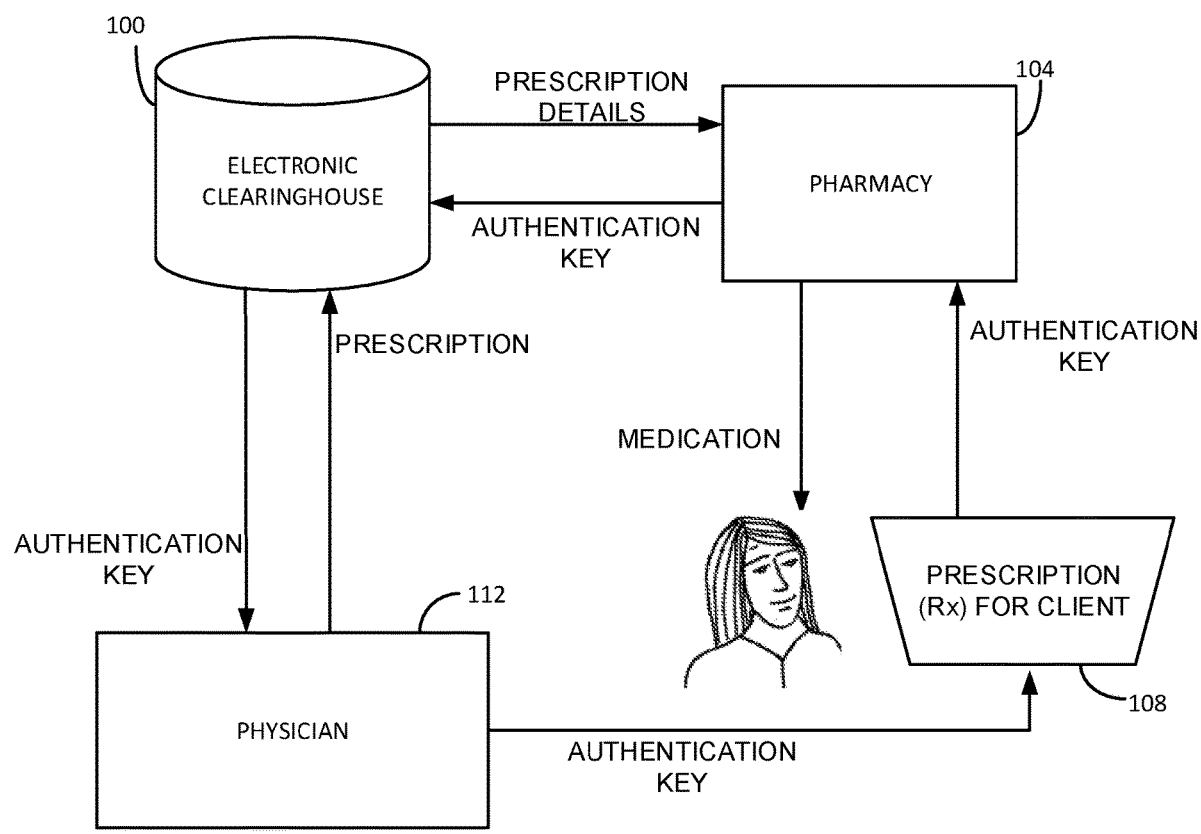
FIG. 1 is a layout of the prescription interaction consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one, or more than one. The term "plurality", as used herein, is defined as two, or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an exemplary embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

Reference herein to "machine-readable code" refers to a machine-readable code such as a QR-Code consisting of an array of visually encoded data fields, typically used for storing URLs or other information for reading by the camera on a smartphone.

Reference throughout this document to "blockchain" refers to a distributed database that maintains a continuously-growing list of data records secured from tampering and revision. It consists of data structure blocks which hold both data and programs. Each block within the blockchain holds batches of individual transactions and the results of any blockchain executables. Each block contains a timestamp and a link to a previous block.

The Authentication/Prescription Key—The Authentication or Prescription Key is a unique key that identifies the Prescription. It is encrypted and can be used to retrieve Prescription information when properly authenticated. It is requested of the Prescription Messenger (PM) by the Prescriber and returned by the PM to the Prescriber, but never directly to the Patient. The Patient may also submit the Prescription Key to the Pharmacist to retrieve the Prescription. The Pharmacist is responsible for authenticating the Patient. To aid in data entry and reduce errors, a bar code will be printed with the Prescription Key.

The Drug Key—The Drug Key is a unique key that identifies the Drug Name, Format, Size and Quantity. It contains no personal private information about the Patient or the Prescriber. The Drug Key is generated by the Drug Prescription Server.

The prescription pricing messenger in an exemplary embodiment may increase physician and patient access to any pharmacy without the need for a pre-selected choice in the process of filling prescriptions and preparing a cost comparison for prescribed medications, using an electronic communications medium and while preserving the security of both the prescription and client. When a patient visits a physician and the physician determines a patient need for a medication, the physician will create a prescription for that patient by establishing communication with an electronic clearinghouse dedicated to the secure creation and management of prescription services to physicians and pharmacies. In addition, a patient may be presented with cost comparison information regarding the medication specified in the prescription and may inform the patient as to the most cost-efficient medication price available for purchase. In the exemplary embodiment a physician first authenticates with the clearinghouse that they are registered with the electronic clearinghouse, that their identity is valid, and that they are legally entitled to generate prescriptions. Upon registration a physician may receive a personal encryption key generated by the electronic clearinghouse and transmitted to the physician. Once authenticated, the physician will be allowed to create or update a prescription record. After prescription data is created, the clearinghouse generates a randomized unique identification code for the prescription and the authentication key is returned to the physician from the clearinghouse.

The prescription authentication key can then be printed containing information related to the patient, the physician, and the unique identification code. The data for medication and dosage is explicitly omitted to prevent filling of the prescription without first authenticating with the clearinghouse. The physician then provides the prescription code to the patient, if the prescription code containing a drug key has not already been provided directly to the patient, and the patient may later have the prescription filled at a medication dispensation facility of their choice, such as a pharmacy, hospital, or other licensed facility.

In this exemplary embodiment, a drug key is a unique key that identifies the drug name, format, size, and quantity. The drug key contains no personal or private information about the patient or prescriber. The drug key is generated by a Drug Prescription Server (DPS) and is composed of four sections, each of varying lengths, with each of the sections separated by a field separator. The format is:

[DC][FS][RX][FS][DR][FS][PT]

where DC is the unique drug code assigned to the medication to be dispensed, FS is the field separator used to indicate the termination of the previous section, RX is the prescription identifier, DR is the code assigned to the doctor or entity prescribing the medication, and PT is the unique patient identifier. In this embodiment, each field in the authentication key also contains a field identifier which permits the rearrangement of the order of the fields within the authentication key. The authentication key is complete when the DC, RX, DR, and PT fields are included in the authentication key, regardless of the order of the sections within the authentication key. The field separator is defined as a character that cannot occur in any of the sections, such as, in a non-limiting example, a special punctuation character that does not occur naturally in the lexicon of values that are permitted for the DC, RX, DR, and PT sections. Additionally, once all sections of the authentication key have been filled in with valid values, the authentication key will be encrypted and converted to Base 64 such that the authentication key is composed of hexadecimal characters only.

In a non-limiting example, the drug key may be available to a patient through a link embedded in a notification sent to a patient. The drug key is encoded plain text, but it is not encrypted. The Drug Code within the drug key may start with a letter rather than a number. This prevents the Drug Code from being interpreted as a phone number on a mobile device. Clicking on the link embedded in the notification received by the patient will retrieve pricing information for prescriptions associated with the patient.

In an alternative embodiment, if clicking on the link does not retrieve the drug pricing for the patient, the patient may open a Drug Pricing Application on a mobile device, or a web page containing a link to the drug pricing application on a computer or mobile computing device or smart phone. After opening the drug pricing application, the patient may manually enter the drug information, including the drug name, strength, format, and quantity, into the application. In a non-limiting example, such a query may take the format of:

Drug1, 500 mg, tablets, 30 count as a complete query entry. The patient may then retrieve a notification transmitted in response to the query that contains the drug key, where the notification may be sent to the patient as a text message, email message, instant message, or any other electronic notification means. In an additional embodiment, the notification message may be printed by the prescriber and manually given to the patient for later use.

In an exemplary embodiment, a Drug Pricing Server (DPS) responds to queries for drug pricing information. The DPS maintains a database of current drug pricing information for all drugs at all pharmacies and dispensing locations in the United States. In this embodiment, the DPS does not require validation of the individual requesting pricing information and does not require any patient information. To receive pricing information and/or drug fulfillment locations nearest to the patient, at a minimum, the patient must enter the drug name into the query sent to the DPS. The search for pricing information may be enhanced by the input of information about drug format, size and quantity. The patient may also input more than one drug for which pricing is desired with a single query.

In this embodiment, the patient may choose to use the location stored in the patient's profile data, location data from a GPS location service, or enter an address containing at least a ZIP code. The location information, in combination with the basic drug information will then be passed to a Drug Pricing Server (DPS). The DPS will return the drug pricing information and the pharmacy location that is nearest to the patient's location as entered into the system or determined by the location service in use. The search and determination of the closest pharmacy can be restricted to a given radius from the patient's current location as defined above. If the patient has provided insurance information as a part of the patient profile stored with the clearinghouse, the DPS may also provide comparative costs for the one or more medications to the medical provider. Regardless of the entry of insurance information, the DPS will always return the drug price and a comparison price for a generic of the drug requested in the query, if available. Additionally, the DPS may return results for multiple location demographics, such as pharmacy nearest home, nearest the office, or nearest to medical practice location for the prescribing medical provider.

In an additional embodiment, patients may still access the functions of the DPS without installing the Drug Pricing Application (DPA) on their smart phone, tablet, internet computer, or other mobile device. The DPA is a native mobile device-based application that may be installed and used on mobile devices having iOS, Android, Windows CE, and other mobile device operating systems. In this embodiment, the patient will be directed to a web page on the DPS. The patient will be provided with the opportunity to download the DPA to their mobile device, or continue to use the web browser. The DPA receives drug information input from a patient through the patient's mobile device. The input may be performed manually by the patient on the keypad incorporated in to the mobile device, or may be transmitted by the selection of a link in a text message or email received by the mobile device. The DPA then queries the DPS database for drug pricing information and returns the requested information to the DPA for display on the mobile device.

In an additional embodiment, the patient may authenticate with the Drug Pricing Cloud Server (DPC) through the web interface and enter the authentication key provided to the patient by their medical service provider. The DPC is an optional server that hosts patient personal and insurance information. The patient personal and insurance information is entered into the DPC when a patient creates an account to use the DPC. After account creation, the patient authenticates their identity with the DPC at the beginning of each session of use to access drug pricing information specific to their medication prescriptions.

In an alternative embodiment, patients or users who do not choose to install the DPA, or who are using a web browser, may interact with the system through the use of a Drug Pricing Web Application (DPWA). The DPWA is a web device-based application that receives drug information input from a patient from a web browser interface to the application. To initiate this application, a user will be directed to a web page on the DPS when interacting with the system using a web browser. Mobile device users will be prompted to download the native application (DPA) or continue with a web browser on the mobile device. In this embodiment, the user selects the option to use a web browser and not to download the DPA. Using the features of the Drug Pricing Web Application (DPWA) requires that the user be registered with the DPS and clearinghouse. If the patient is not currently registered with the clearinghouse and DPS system, they will be provided with an opportunity to register. If the patient chooses not to register with the system, they may only access drug or medication pricing information by manually entering the names of the drug(s) and medication(s) and the patient's current physical location into the DPWA. Whether the patient chooses to register with the system or not, the patient must still provide authentication information to verify the patient's identity to the DPCS to access the system. If a patient registers with the DPS system and the clearinghouse upon authentication of identity the DPS system will generate a personal encryption key and transmit this personal encryption key to the patient.

Following authentication, to receive pricing information and/or drug fulfillment locations nearest to the patient, the patient may choose to use the location stored in the patient's profile data, location data from a GPS location service, or enter an address containing at least a ZIP code. The location information, in combination with the basic drug information will then be passed to a DPS. The DPS will return the drug pricing information and the pharmacy location that is nearest to the patient's location as entered into the system or determined by the location service in use. The search and determination of the closest pharmacy can be restricted to a given radius from the patient's current location as defined above. If the patient has provided insurance information as a part of the patient profile stored with the clearinghouse, the DPS may also provide comparative costs for the one or more medications. The pricing, location, and price comparative (if returned) information is returned by the DPS to the DPWA and presented on to the patient on the web screen display managed and updated by the DPWA.

In each embodiment, patient personal and insurance information can be stored in the cloud to be accessible either through the DPA or the DPWA.

In the exemplary embodiment, no pharmacy is pre-selected in the process. After receiving the prescription with embedded prescription code from their physician, the patient may take it to a pharmacy of their choosing. The only caveat is that the pharmacy must subscribe to the electronic prescription clearinghouse. The pharmacy may have been located for the patient through the use of the DPA or DPWA location service. When a pharmacy that subscribes to the clearinghouse receives the prescription, the pharmacy will then authenticate with the clearinghouse to access the patient's prescription using the unique prescription identification code.

In this embodiment, the prescription clearinghouse calls the DPS once the medication is read from the patient's prescription after the prescription has been accessed by the clearinghouse. The DPS maintains a database of current drug pricing information for all drugs and medications at all pharmacies in the United States. The DPS does not require, and will not access, patient information. The data required by the DPS includes the drug or medication name, the format of the drug, size and quantity, however, the DPS requires the drug or medication name at a minimum to perform a drug pricing comparison. Including the drug or medication format, size and/or quantity will enhance the search for the drug or medication in the drug pricing database. The DPS may also accept multiple drug pricing requests in a single batch pricing request.

The DPS returns both drug-pharmacy availability and pharmacy-price whenever a location is provided by a Global Positioning System (GPS) location service or when the location is supplied manually with an address containing at least a ZIP code. The DPS may return results for more than one patient demographic, in a non-limiting example, the demographic may be for a patient home, work, or practice location. In addition, the DPS will always return comparison pricing for generic alternatives versus brand name drugs or medications (where available) for registered users, regardless of the drug or medication being researched. In this exemplary embodiment, the Prescription Messenger clearinghouse and the DPS will share the same drug or medication database.

Once accessed, the prescription data is flagged as having been either filled or invalidated by the clearinghouse and is no longer available to other pharmacies. If the pharmacy with access to the prescription data has the medication on hand, the pharmacy may then fill the prescription for the patient. If the pharmacy with access does not have the medication on hand, it may return the prescription code to the clearinghouse so that the prescription may be filled by another validated pharmacy.

In this exemplary embodiment, filling a prescription through the use of the prescription messenger allows a physician to create prescriptions through the electronic clearinghouse that preserve the privacy of the patient and the type and amount of any medication they are taking. In addition, the prescription messenger provides patients with the flexibility of choosing any pharmacy that subscribes to the electronic clearinghouse for filling their prescription. The prescription messenger also provides a mechanism for pharmacies to access prescription data and automatically update prescription status in a forum that is accessible to all subscribing physicians and pharmacies, as well as, allowing pharmacies to perform a quick query to inquire about the basic prescription parameters, such as medication and dosage, to provide for a verification against pharmacy inventory prior to dispensing any medication.

In an embodiment the clearinghouse and DPS require the physician to log into a protected account on a centralized server. The clearinghouse and DPS may be cloud-based and accessible by the physician only after the physician provides a password or other credentials. The clearinghouse and DPS may be hosted on a first cloud-based server, referred to herein as, "Cloud One."

In an embodiment, a Prescription Encryption Application (PE) may be hosted on a second cloud-based server, referred to herein as "Cloud Two." The PE has accounts associated with particular prescribing physicians. A Client Application (CA) may be used upon a user's desktop or mobile device such as, by way of non-limiting example, cell phone, smart phone, laptop computer, desktop computer, or tablet. In this embodiment, a patient may use the CA to register a patient-specific physician-associated account with the PE in Cloud Two. To register, the patient provides certain proof of identification such as, by way of non-limiting example, a passport or social security card. Upon the patient's having registered, the PE issues a Unique Encryption and Decipher Key to the patient, such Unique Encryption and Decipher Key being associated with the patient's individual CA. Each Unique Encryption and Decipher Key is unique to the patient for whom it is generated and with whom the Key is associated.

In an embodiment, the patient's CA is capable of generating time-sensitive encrypted machine-readable code keys using any number of patient-specific parameters, such as, in a non-limiting example, a QR-Code key. The time-sensitive encrypted machine-readable code key generated is signed by a Cloud 2 signing authority. These parameters may include, but are not limited to, any combination of the patient's name, address, phone number, social security number, or insurance information. The default life-span of any generated Machine-readable code key is pre-configured by the system and may be updated or changed by the system administrator or other authorized person, including the patient if authorized. The default Machine-readable code key life-span may be measured in minutes, hours, or days rather than being of permanent duration. The physician may generate a time sensitive prescription code that is associated with any prescription generated for a particular patient. This time sensitive prescription code provides for additional security as the prescription will become invalid if not fulfilled within the time period specified. The life-span of any generated machine-readable code and/or any generated prescription code may be pre-configured for a specific time length, or may be pre-configured based upon an exterior event such as the delivery of the machine-readable code to the patient as a time-offset from that event, where the time-offset may be pre-set as a particular time span. The patient will have downloaded and registered his or her own client application and personal identity prior to visiting a physician or pharmacy.

In an embodiment, when a patient has an appointment with a physician where a prescription is about to be prescribed, the patient uses the patient's own CA to generate a unique encrypted machine-readable code key using such information as, by way of non-limiting example, the patient's name, address, date of birth, and insurance information. This machine-readable code key refers to the patient provided information and is tied to the name of the prescribing physician. Patient use of the machine-readable code further anonymizes any prescription fulfillment the patient may pursue.

The patient then shares the machine-readable code key with the physician, and the physician stores the machine-readable code key in the physician's account in the PE Application. Once the physician uploads the machine-readable code key to the PE Application in Cloud Two, the PE Application contains a record of the encrypted machine-readable code key's having been generated by the patient for the purpose of referencing a particular Prescription. In this context, the term "Prescription" refers to a particular drug being prescribed by a specific physician at a certain dose, such dose to be taken by a particular patient upon a certain schedule. The PE Application is able to associate information including but not limited to the patient's name, address, date of birth along with the physician's name in the patient record maintained within Cloud Two and signed by a Cloud two signing authority.

In an embodiment, when the patient presents a prescription for fulfillment at a pharmacy to have the Prescription filled, the patient presents the machine-readable code key as identification. The pharmacy staff member then scans the machine-readable code key and validates the prescription through the DPS on Cloud One. The patient's Cloud One DPS account will reference the machine-readable code Key on Cloud Two and confirm the existence of a valid prescription. The pharmacy may then dispense the prescription.

In an embodiment the machine-readable code key contains no readily-identifiable patient information. In an embodiment, the machine-readable code key is accompanied by pricing information for both generic and name brand versions of a prescribed drug. Such prescription pricing information may be time-limited.

In the event of attempts to refill the prescription, the PE on Cloud One will retain all refill data for a specific prescription, and may communicate prescription status information to the patient's CA. When the patient requires a prescription to be refilled or when the pre-configured time span specified at creation of the machine-readable code key has expired, the patient will cause the CA to generate a new encrypted machine-readable code key that references a refillable prescription and the prescribing doctor information.

In the event that a patient does not have access to a mobile or desktop device upon which to use the CA, a different embodiment is employed. In such embodiment, the prescribing physician may generate a machine-readable code key on the physician's own device on behalf of the patient. The prescribing physician then transmits the newly encrypted machine-readable code key to the PE on Cloud Two. At the same time, the physician sends a unique prescription-referencing code to the DPS on Cloud One. The physician may then print the encrypted machine-readable code key for the patient to present at a pharmacy.

In an embodiment, to provide extra security all records on Cloud One and Cloud Two may be hashed to form a blockchain in each of Cloud One and Cloud Two to provide for transactional and data security. In an embodiment, a blockchain capable secure encryption system process may begin with the acceptance of one or more information files from a user. Transaction and other data are stored as entries into blocks maintained within the respective cloud. When a block is filled based upon a pre-determined block entry length, the block is closed and the closed block run through a hashing algorithm to create a hash identifier for that block. This hash identifier is then entered as the first data field entry into the subsequent block, followed by transactional and other data as the data is received by the cloud. The information file representing a block or a chain of blocks may then be compressed to reduce the overall size of the file to be encrypted if encryption is desired. However, compression is not a requirement prior to encryption. If the user requires greater time sensitivity, compression of the information file may be omitted.

In this exemplary embodiment, the information file, whether compressed or uncompressed, may be encrypted utilizing any encryption cipher or methodology preferred by the user. The system may utilize any encryption cipher or method such as public/private key, Pretty Good Protection (PGP), RSA, or any other encryption method in use by the information file owner. Choosing the encryption methodology permits the owner to share the encrypted file with any other authorized user. In this exemplary embodiment, the file hash of the encrypted file, previously created, is gathered and utilized as the file name of the grid table portion of an echo key table to be created for each information file. The grid table portion may then be created with the file name hash from the originally submitted information file. As a portion of this step, the system also gathers the original information file name and file size.

In this exemplary embodiment, after the creation of the grid table portion, the information file is sliced into segments of about the same size. The segments are catalogued in the grid table portion with each segment having a segment number, segment hash ID, and information file name. In this fashion each segment is identified with a particular information file. The grid table portion records the segment as coordinates of a table via both the information file hash and the segment hash as coordinates of the segment. Upon completion of the grid table portion, the segments and grid table portion are scheduled to the designated blockchain for the user information file. At this point in the process, all information files are encrypted, incorporated within one or more blockchain structures, and stored in a distributed database.

In an embodiment, reconstruction of one or more information files begins through the submission of a grid hash table associated with an information file and the information file name to a system server. The system server transmits the encrypted grid table to a user. The user decrypts the grid table using the pre-arranged encryption cipher or method, and submits the decrypted segment names and hash values to the system server to permit the system server to retrieve the segments from the electronic databases into which the segments have been distributed. The segments are then reassembled following the order and relationships recorded in the grid table. The segment reassembly produces the original encrypted information file.

The system server utilizes the user signature to decrypt the original encrypted information file. If the encrypted information file was compressed, the system server will perform a decompression action on the information file. If the encrypted information file was not compressed, the system server may skip this step in the process. The information file is tagged with the original information file name retrieved from the grid table. The reconstituted and decrypted information file may then be verified using the check hash originally generated from the information file prior to entering this process.

Turning now to FIG. 1, in an exemplary embodiment the implementation of the prescription messenger is presented at a level of communication interaction between the components of the system as a whole. A prescription 108 is generated by a physician 112 for a patient upon the patient's visit to the physician. Prior to generating the Prescription 108 the physician 112 establishes communication across a secure communication channel with an electronic clearinghouse 100 established to manage the interaction for the creation and management of a large number of Prescriptions. Once the physician 112 has contacted the electronic clearinghouse 100, the physician 112 must provide information to the electronic clearinghouse 100 to validate the physician 112 as authorized to generate prescriptions without restrictions, or, if restrictions apply, the authorization is set at a level of prescriptions the physician 112 is authorized to generate. The physician 112 enters the relevant authentication information and submits it to the prescription messenger. The prescription messenger server validates the information and, upon successful information entry, allows the physician 112 to access the prescription messenger server. After the physician 112 has been successfully authorized, he/she transmits the information required to create a valid Prescription.

Upon receipt of the Prescription information, the electronic clearinghouse 100 generates a Prescription identifier code and transmits this Prescription identifier code to the physician 112 across the same secure communication channel. The physician 112 then provides the Prescription code to the patient. The Prescription code does not contain any patient information, thus decoupling the Prescription from the patient through the use of the Prescription code. This decoupling of Prescription information from patient information assists in maintaining the privacy of the patient. Additional privacy and security concerns will be discussed later in connection with further non-limiting embodiments of the system.

In a further embodiment, the physician 112 may also present the patient with drug and medication pricing information. To obtain drug pricing information, the prescription messenger server at the request of the physician 112, sends the drug or medication information to the DPS. Upon receipt of the request, the DPS retrieves the drug key(s) for the requested drug and medications to the prescription messenger. The prescription messenger server generates the Prescription code and returns both the Prescription code and the drug key(s) to the physician 112. The physician 112 may now provide both the Prescription code and the drug key (s) to the patient.

In a further embodiment, the patient is now free to take the Prescription code to any pharmacy 104, or other facility such as a hospital or discount store having a license to dispense Prescriptions, that is enrolled with the electronic clearinghouse 100. Personnel at the pharmacy 104, upon receipt of the Prescription code from the patient, establish communication over a secure communication channel with the electronic clearinghouse 100 and provide credentials of their membership. Once authorized, the pharmacy 104 may transmit the Prescription code to the electronic clearinghouse 100. The electronic clearinghouse 100 validates the Prescription code and returns the Prescription 108 information to the pharmacy 104, allowing the pharmacy 104 to fill the Prescription 108 and provide the medication to the patient.

Figure 2:
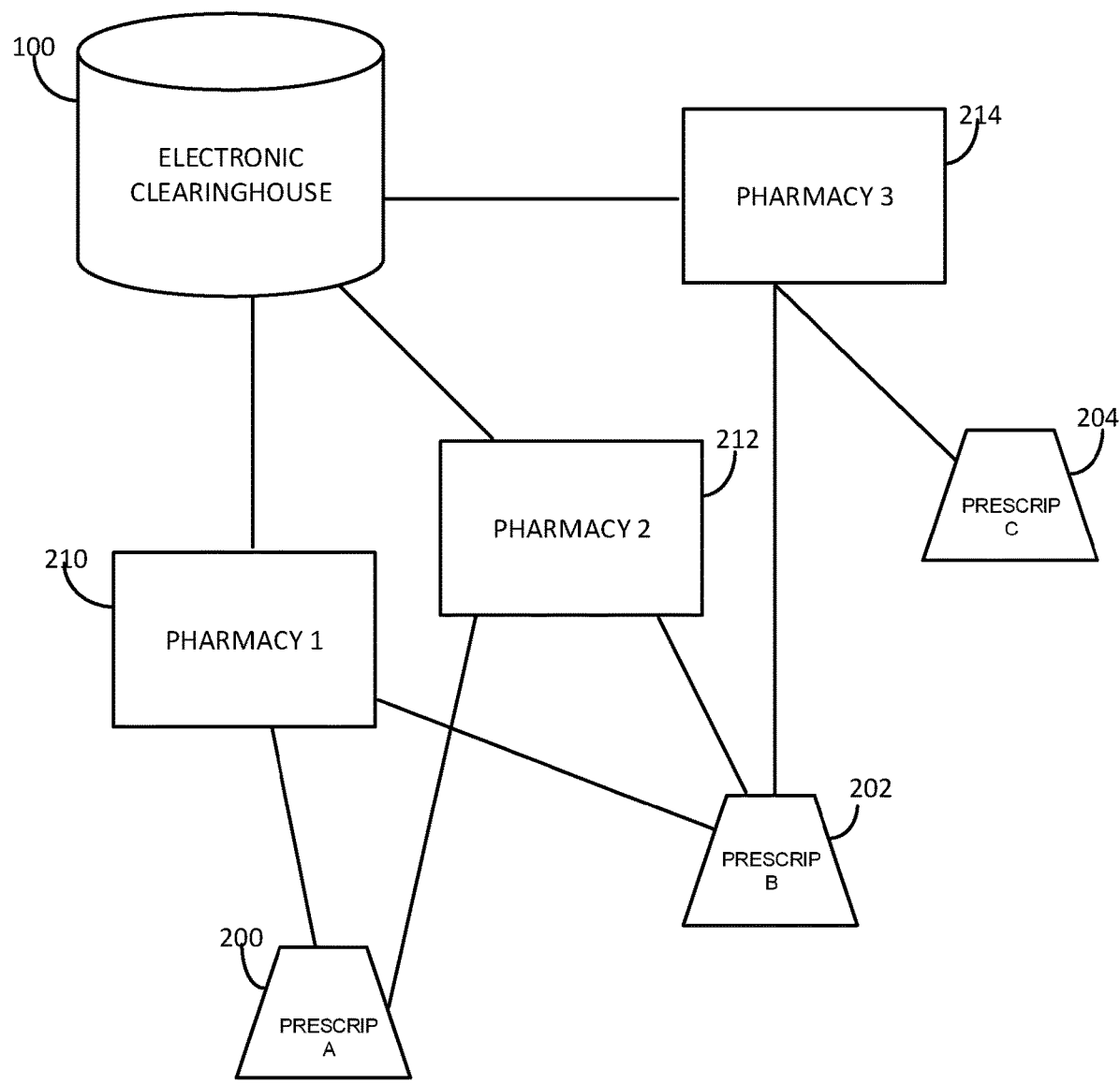
FIG. 2 is a view of prescription message traffic between the patient, pharmacy and an electronic clearinghouse consistent with certain embodiments of the present invention

Turning to FIG. 2, in an exemplary embodiment each Prescription 108 generated by a physician 112 authorized through the electronic clearinghouse 100 may be presented for fulfillment at any pharmacy (104, 210, 212, 214) that is enrolled with the electronic clearinghouse 100. In this embodiment, since the Prescription code does not provide any data connection between the patient and the Prescription 108 information until presented at the electronic clearinghouse, the freedom to present an Prescription code at any enrolled pharmacy (210, 212, 214) provides the patient with data privacy with regard to the Prescription 108 should the Prescription code become lost. In addition, if a pharmacy (104, 210, 212, 214) does not have the appropriate medication, or does not have the appropriate amount of medication, on hand to fulfill the Prescription 108, the patient is free to take the Prescription code to another enrolled pharmacy (210, 212, 214) for fulfillment with data security intact. In this embodiment, Prescription codes (200, 202, 204) may be presented at any of a plurality of pharmacies (210, 212, 214) for fulfillment. If, in an example of a possible scenario, Prescription code B 202 were to be presented for fulfillment to pharmacy 1 210 and pharmacy 1 210 did not have the medication on hand, the Prescription code would be returned to the patient. The patient would then be free to present the Prescription code to pharmacy 2 212. If pharmacy 2 212, in this non-limiting example, were not able to fulfill the Prescription 108 for any reason, the code would be returned to the patient and the Prescription code could then be presented for fulfillment at pharmacy 3 214. The patient is assured that, since the Prescription 108 details are managed and communicated between the electronic clearinghouse 100 and the pharmacies (210, 212, 214), their personal information is never exposed outside of the pharmacy, and, if the Prescription code is lost, a finder of the Prescription code may not use the Prescription code to learn anything about the patient, or clandestinely receive the patient's medication instead of the patient.

Figure 3:
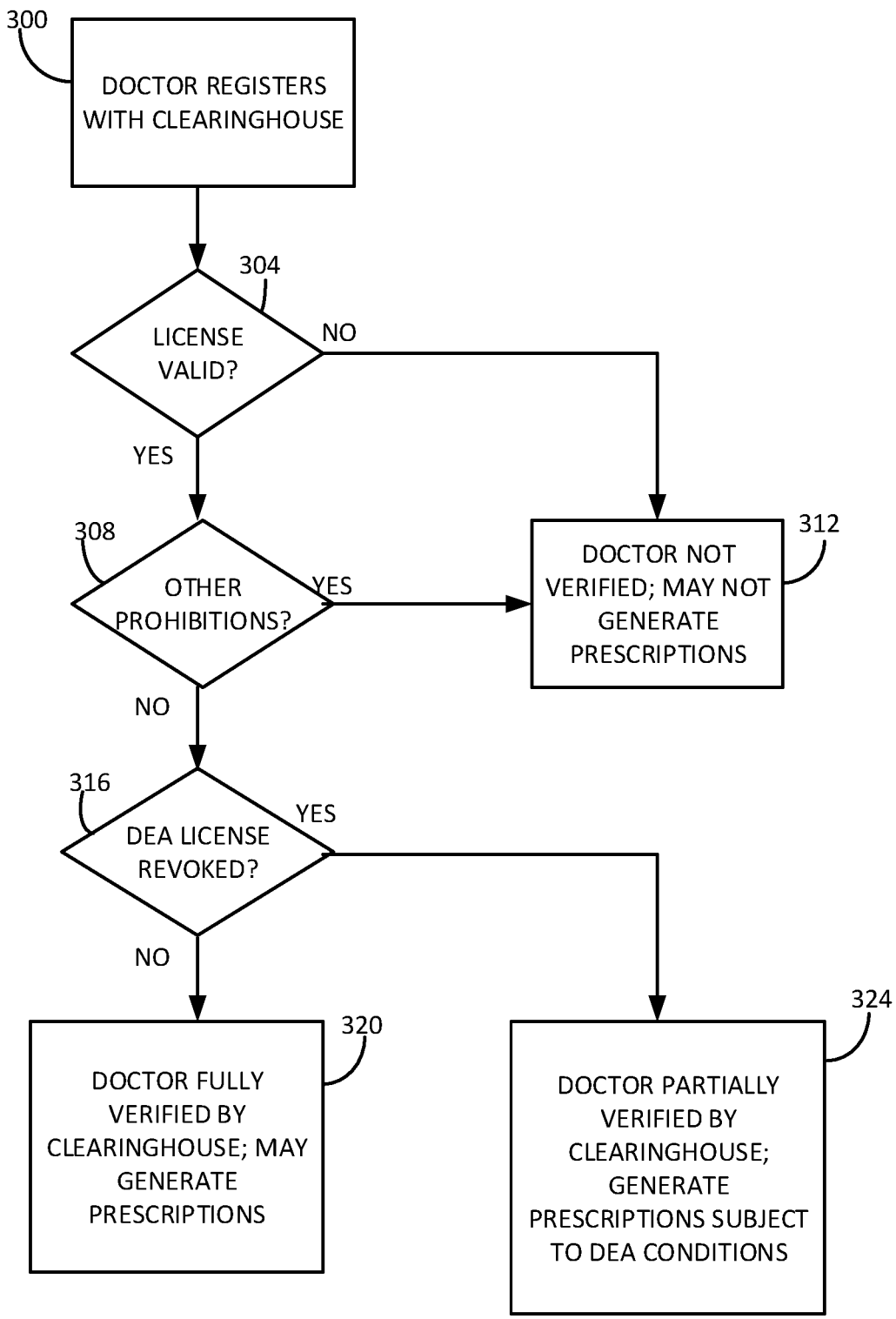
FIG. 3 is a flow layout of doctor validation with a prescription clearinghouse consistent with certain embodiments of the present invention.

Turning now to FIG. 3, the process of the validation of a physician 112 with the electronic clearinghouse 100 is discussed within an exemplary embodiment. As an initial condition, the physician 112 registers with the electronic clearinghouse 100 and provides credentials for validation 300. The electronic clearinghouse 100, as a primary area of responsibility, will seed to validate the credentials provided by the physician to ensure that the physician 112 has a current and valid license 304 to dispense medication. If the physician 108 cannot be validated for any reason, the electronic clearinghouse 100 will place an internal notification in association with that physician's name that the physician 108 is not authorized and may not generate Prescriptions 312. The electronic clearinghouse 100 performs this authorization and license validation activity each time a physician is added to the clearinghouse data store, and manages this data for relevance on an ongoing basis such that the authorization of a physician 108 in maintained as currently as possible.

As part of the validation, the electronic clearinghouse 100 is also responsible to determine if there are other prohibitions 308 against the physician 108 seeking to register with the electronic clearinghouse 100. Other prohibitions may include temporary revocation of a physician's license for disciplinary reasons, permanent revocation of the physician's license, or any other manner in which licensure has been suspended or revoked by the state authority charged with maintaining physician licenses. If other prohibitions exist 308, then the physician 108 cannot be authorized by the electronic clearinghouse 100 and the physician will not be allowed to generate Prescriptions 312 through the electronic clearinghouse 100.

In addition to licensure revocation, the electronic clearinghouse 100 will validate the physician 108 for license restrictions. In a non-limiting example, the electronic clearinghouse will seek to determine whether the Drug Enforcement Agency (DEA) has revoked the physician's license to prescribe narcotics 316. If the physician's license has been revoked by the DEA, the physician may still be authorized to prescribe other medications. Thus, in this non-limiting example, the electronic clearinghouse 100 will partially authorize the physician to generate Prescriptions, with the prohibition that the physician 108 may prescribe medication subject to DEA conditions 324.

After the electronic clearinghouse 100 has completed the validation of the physician's credentials, and determined that there are no revocation or restriction actions against the physician 108, the physician 108 is authorized by the electronic clearinghouse 100 to generate Prescriptions 320 and the electronic clearinghouse 100 may generate a personal encryption key for the physician and transmit the generated personal encryption key to the physician for future use.

Figure 4:
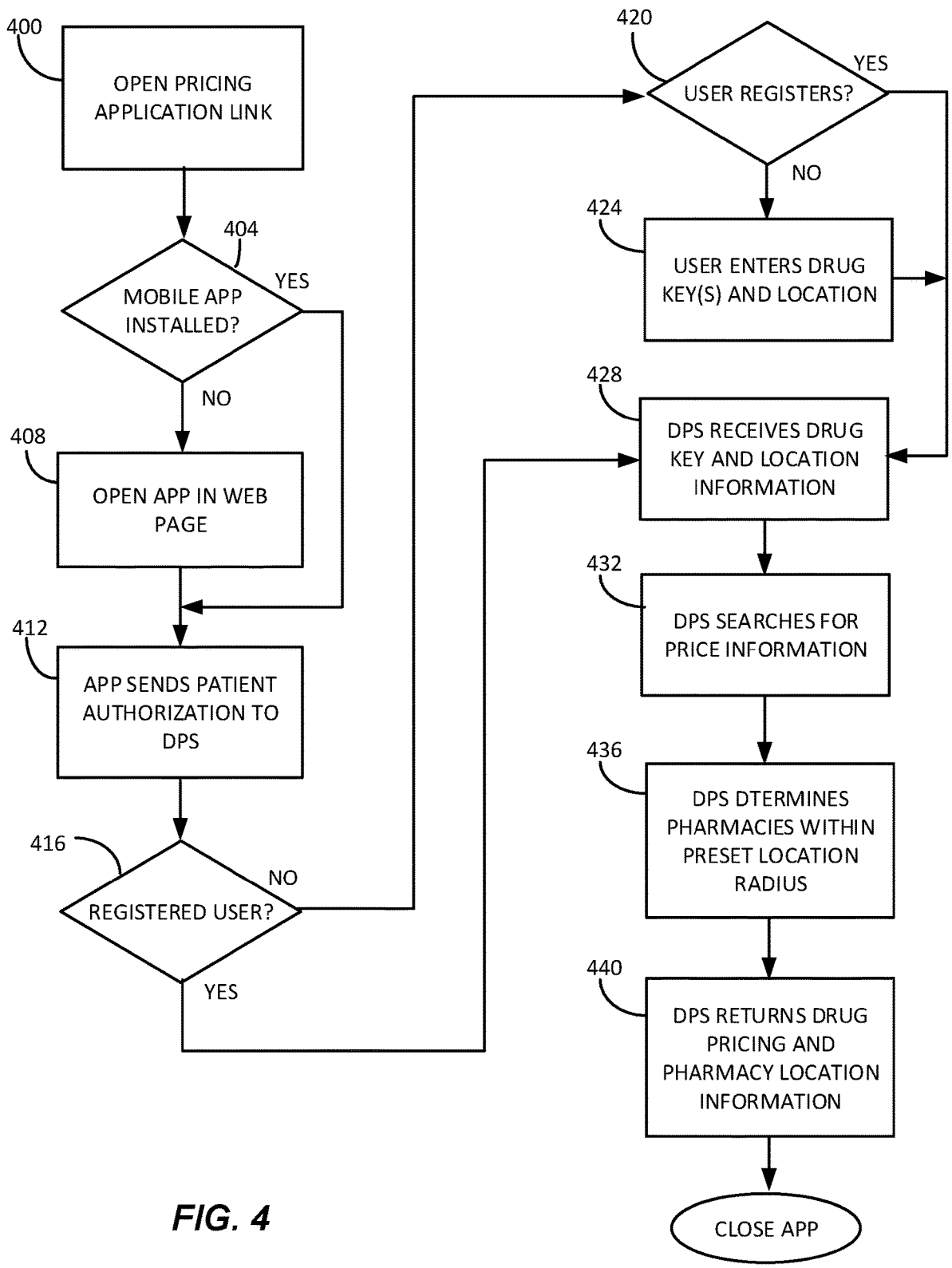
FIG. 4 is a flow layout for the determination of pricing and location information with delivery to a mobile device consistent with certain embodiments of the present invention.

Turning now to FIG. 4, at 400, a patient may receive pricing information for the prescription they have been issued by initiating a prescription pricing application on a mobile device, such as a mobile phone, smart phone, tablet, internet computer, or other internet connected mobile device. The patient may receive one or more drug keys from the prescriber when the Prescription is initially generated. Alternatively, the patient may receive the drug key(s) through additional modes of communication from the prescriber.

In an alternative embodiment, the patient may receive an email or other message from their medical provider containing one or more drug key(s) and an embedded link to a prescription pricing application. The patient may then select the link in the email message. At 404, if the patient has installed a prescription pricing mobile application on their mobile device, selecting the link in the email will open the mobile application on their mobile device. If the patient has not installed the prescription pricing mobile application on their mobile device, selecting the embedded link in the email or other message from the medical provider will open a prescription pricing application in a web browser page on the mobile or other device 408.

In this embodiment, whether the patient opens the prescription pricing application in a mobile application or in a web browser page, the application will accept input of the prescription authorization key from the patient. The application then transmits the prescription authorization key entered by the patient to the drug pricing server (DPS) at 412. The DPS examines the status of the patient to determine whether the patient is a registered user of the prescription pricing application. At 416, if the patient is not a registered user of the prescription pricing application, the patient is given an opportunity to become a registered user at 420. Should the patient choose not to become a registered user of the prescription pricing application, the user may not access all the features of the prescription pricing application, but may still receive prescription pricing information by entering the drug or medication name, or the drug key(s) received from the prescriber, and the current patient physical location by entering at least the ZIP code of the patients current physical location when prompted at 424.

If the patient is a registered user of the prescription pricing application, the DPS receives drug or medication information and the physical location information, as reported by the GPS, ZIP code, or other location information, directly from the database shared with the prescription messenger system application at 428. If drug pricing information is desired, the DPS will also receive drug key(s) with the message from the prescription messenger application. The patient may then receive drug pricing information from the DPS. If the patient has instead entered the drug name and physical location into the mobile or web application input page, the DPS uses the entered drug name and physical location at 428. The DPS uses the drug or medication name and the physical location to search the database shared with the prescription messenger system for price information for the drug or medication at 432. After retrieving the drug or medication pricing information, the DPS next determines the location of all pharmacies capable of dispensing the drug or medication named that are within a pre-set radius of the physical location of the patient 436. It should be noted that the radius may be set to a pre-determined distance, ZIP code or set of ZIP codes, and that the radius may be updated by the patient through interaction with the application to either broaden or narrow the number and location of pharmacies found. At 440, the DPS returns both the drug or medication pricing information and the pharmacy location information to the patient. It should be noted that the pharmacy location information may be returned as textual address information, mapping information, or any other physical location information that may be presented on the display of the mobile device in use by the patient at the time of the query. In an alternative embodiment, the patient may enter two or more drugs or medications and receive pricing information for each of the drugs or medications. Additionally, the DPS may return price comparison information for generic and name brand drugs or medications, as well as price comparison information at different pharmacies within the pre-set radius from the patient location.

Figure 5:
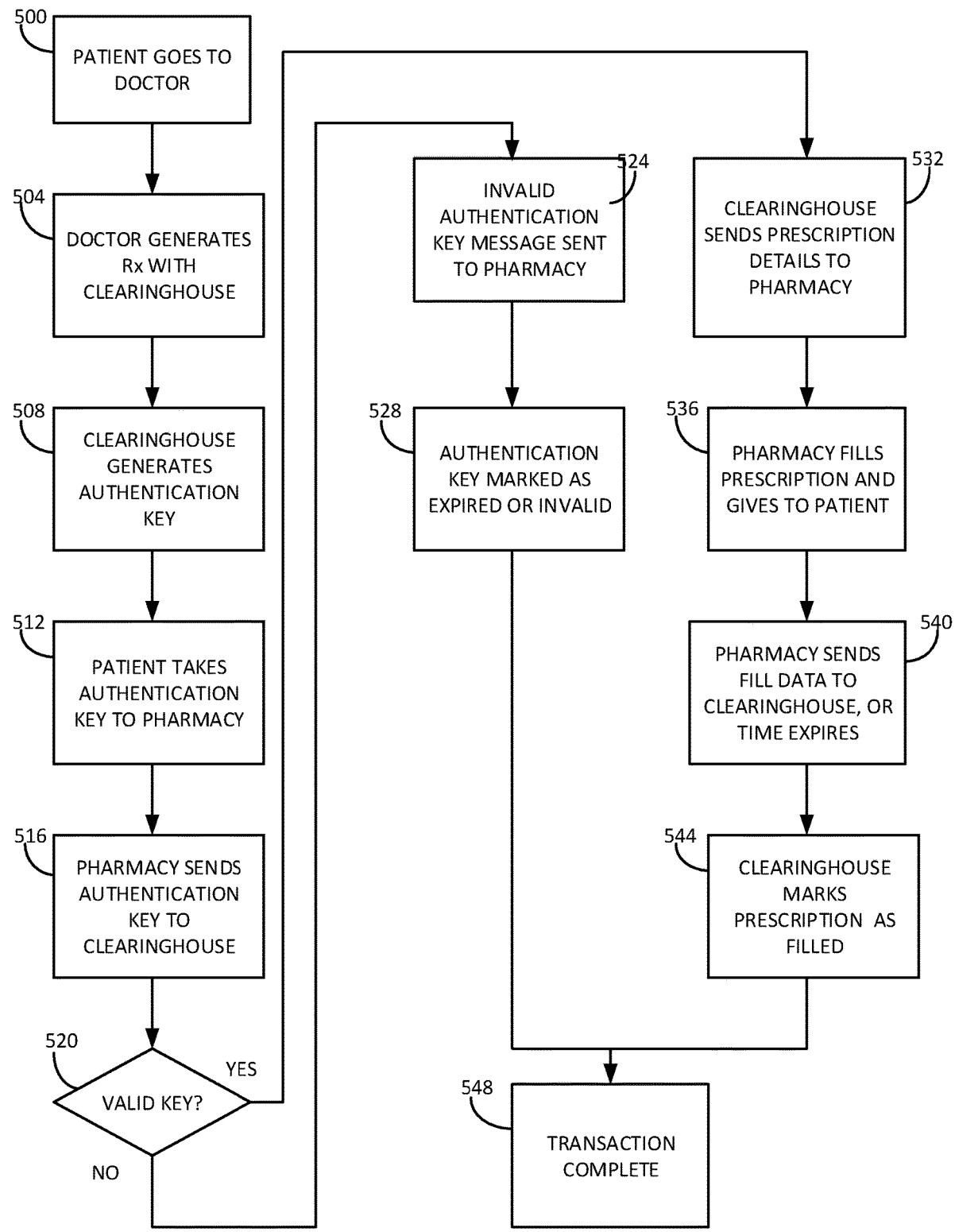
FIG. 5 is a flow layout for the generation and presentation of prescriptions consistent with certain embodiments of the present invention.

Turning now to FIG. 5, an exemplary embodiment for a patient transaction is presented. The Patient visits a physician of their choice 500. The physician has been authorized to generate a Prescription in compliance with the non-limiting example presented in FIG. 3. The physician 108 establishes communication across a secure communication channel to the electronic clearinghouse 100 through the use of a XEOMED™ application, or any other registered 3rd party application or device which can communicate over the internet via a secure connection and exchange electronic messages. The physician 108 enters their authorized Login ID and Password established with the electronic clearinghouse 100. In compliance with the electronic clearinghouse 100 physician licensure update process, the electronic clearinghouse 100 will attempt to validate the physician logon against the updated records of the physician licensure status. The electronic clearinghouse 100 will accept the physician logon if there are no current or pending licensure revocation or restriction actions, and the physician logon data are correct. The electronic clearinghouse 100 will reject the logon attempt if the logon data are incorrect, or if the physician's credentials have been revoked.

Once successfully logged in to the electronic clearinghouse, the physician enters the Prescription information composed in part of patient and medication details and transmits it to the electronic clearinghouse to generate a Prescription 504. The physician 108 may submit Prescriptions individually or as a group of Prescriptions to be generated simultaneously. The electronic clearinghouse verifies with the physician 108 that the correct information was transmitted through a question and response with the physician 108. The electronic clearinghouse 100 verifies that the physician 108 is authorized to write the prescription for the medication specified in the transmission of the details for the prescription. In a non-limiting example, if the physician's DEA license is revoked, he cannot write narcotic prescriptions, or if subject to pending disciplinary action for any other reason, he cannot write prescriptions for any medication. Once validation of the prescription details and the physician 108 are complete, the electronic clearinghouse 100 stores the data for the prescription request in its secure database.

In an exemplary embodiment, the electronic clearinghouse next generates a prescription code in the form of a secure authentication key 508. The authentication key is unique for each prescription request, whether the request is for a single prescription or a plurality of prescriptions are submitted as a group within a single request, such that multiple prescriptions may share the same authentication key. In an exemplary embodiment the authentication key may expire after a pre-determined period of time. In a non-limiting example, the expiration time period could be set for 30 days, or for any time period that experience determines is sufficient for the redemption of the average prescription without causing hardship on the patients. If drug pricing information is requested as well, the prescription messenger application will also submit the drug or medication information to the DPS. The DPS will return the drug key for each drug or medication for which the DPS received drug information.

After the physician 108 receives the authentication key and, if requested, the drug key(s), the physician 108 may print the prescription authentication key, drug key(s) and other prescription information as a prescription code on a regular Prescription pad. The patient information is intentionally omitted from the printed prescription code. In addition to the key, a Bar Code will be printed to simplify the data entry at the pharmacy 104. The patient may then visit the enrolled pharmacy of their choice. In a non-limiting example, the physician 108 may provide the patient with a list of pharmacies nearby that are so enrolled. The patient provides the pharmacy 104 the prescription code with the authentication key 512.

The pharmacy 104 connects to the electronic clearinghouse 100, once again across a secure communication channel such as a network connection with a secure encryption service for data transmissions. The pharmacy 104 is validated by the electronic clearinghouse 100 as being properly enrolled and the pharmacy transmits the prescription code 516.

In an exemplary embodiment, the electronic clearinghouse receives the transmitted prescription code that includes the authentication key and validates the authentication key and prescription 520. The electronic clearinghouse 100, in a non-limiting example, may verify that the prescription requests are valid by checking the prescription code for any data entry errors 524. The electronic clearinghouse may also determine whether the prescription was already filled, has expired, or was never submitted 528.

If the prescription is determined by the electronic clearinghouse 100 to be valid then for each valid prescription, the patient and prescription information is returned to the pharmacy 532. The pharmacy 104 will then fill the prescription using the details transmitted from the electronic clearinghouse 100 and present the medication to the patient 536. The pharmacy 104 may then send a confirmation of the filling of the prescription 540, or may simply move on to the next transaction. If the pharmacy 104 does not send a confirmation of fulfillment, the prescription will be assumed filled by the electronic clearinghouse 100 and the prescription record will be updated as submitted such that the prescription can no longer be filled 544.

In the event the pharmacy 104 is unable to fill the prescription, the pharmacy 104 will notify the electronic clearinghouse 100 that the prescription has not been filled and return the prescription record to the electronic clearinghouse 100. Upon the receipt of this record the electronic clearinghouse 100 will change the prescription status back to "fillable" for any prescription requests that were returned by the pharmacy 104. A log entry will be created at the electronic clearinghouse 100 and within the XEOTECH™ application indicating that the pharmacy 104 attempted to fill the prescription but was unable to do so.

The patient may also use the DPA or DPWA to access pricing information independently from the filling of the prescription. By entering the drug key(s) provided by the prescriber into the DPA or DPWA, the patient may receive drug pricing information on their phone, tablet, internet computer, or other handheld or mobile device.

Figure 6:
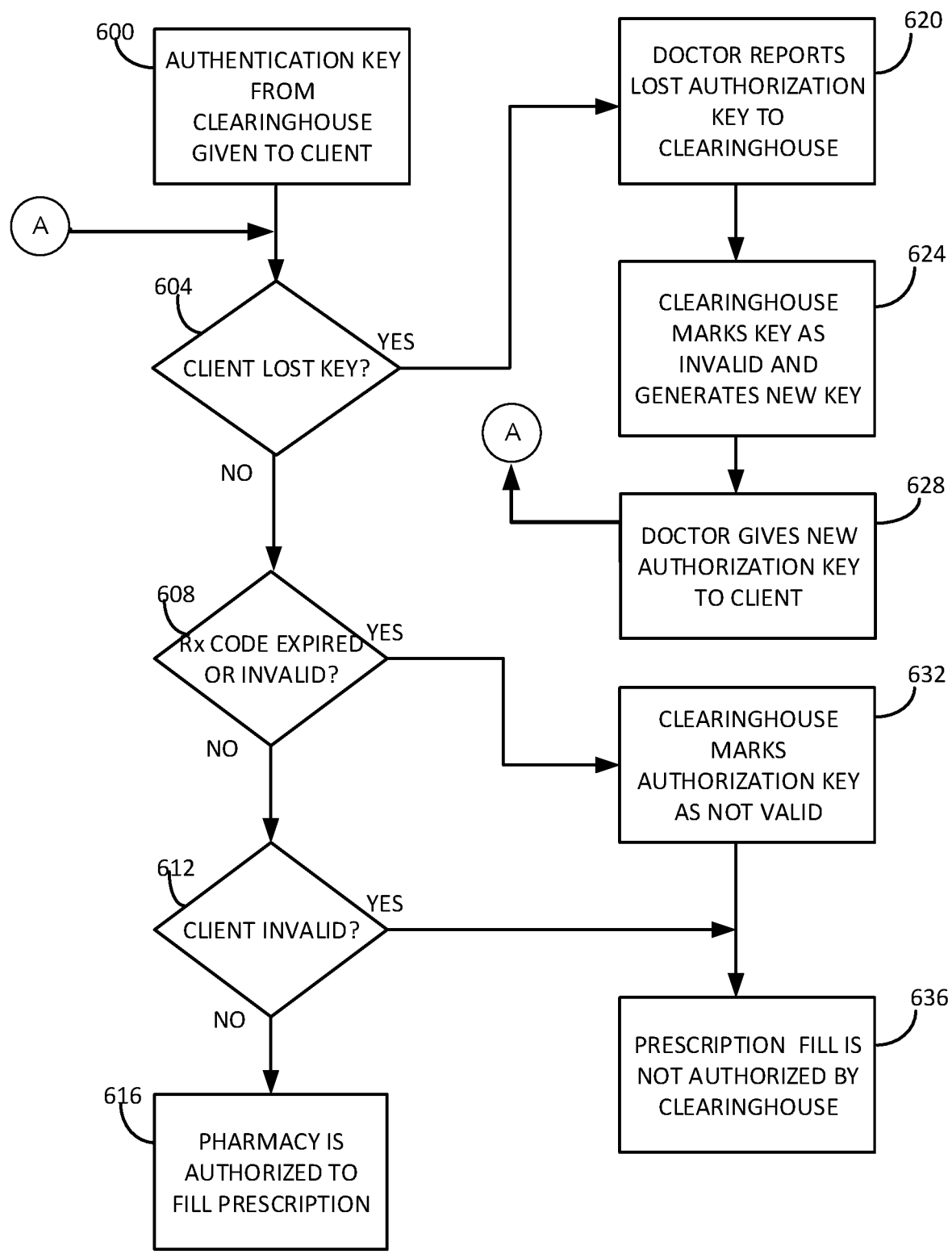
FIG. 6 is a flow layout for the validation of a prescription with the electronic clearinghouse consistent with certain embodiments of the present invention.

Turning now to FIG. 6, this figure presents an exemplary embodiment of the use of the prescription code by the patient. The prescription code is given, printed upon a standard prescription pad form, to the patient 600. If, prior to presentation at an enrolled pharmacy 108, the patient loses the authentication key 604, the patient or the pharmacist must contact the physician 108. The physician 108 may then update the prescription record with the electronic clearinghouse 100 such that the prescription record maintained within the secure data storage within the electronic clearinghouse may be updated 620. The electronic clearinghouse may then void the original prescription and authentication key and issue a new authentication key 624 to preserve the security of the patient's medical information and yet continue to allow the patient the opportunity to fulfill the prescription. The physician 108 may then issue the newly generated prescription code to the patient 628. If the patient loses the authentication key again, they must repeat the process steps beginning with contacting the physician 108 to once again have a new authentication key generated.

Upon presentation to a pharmacy 104, the pharmacy 104 sends the prescription code across a secure communications channel to the electronic clearinghouse 108. Upon receiving a request to fulfill a prescription in which the prescription code and authentication key do not match any existing record in the data storage may indicate that the prescription code is invalid 608. In this instance, the electronic clearinghouse 100 will mark the prescription code as invalid 632 and would not issue prescription details. The electronic clearinghouse will also perform a validation that the patient has a pre-existing record 612 with the physician 108 stored within the secure database in the electronic clearinghouse 100. The lack of a patient record for that prescription may indicate that someone, such as a hacker, is trying to guess an authentication key. If the prescription is determined to be invalid or expired the prescription is not authorized and the electronic clearinghouse 100 transmits a denial, omitting any prescription details except the prescription code originally sent 636. If, however, all validation checks for the prescription code and the patient are verified, the electronic clearinghouse authorizes the pharmacy 104 to fill the prescription 616 and sends the appropriate prescription details, including medication and patient details to the pharmacy 104 for fulfillment.

Figure 7:
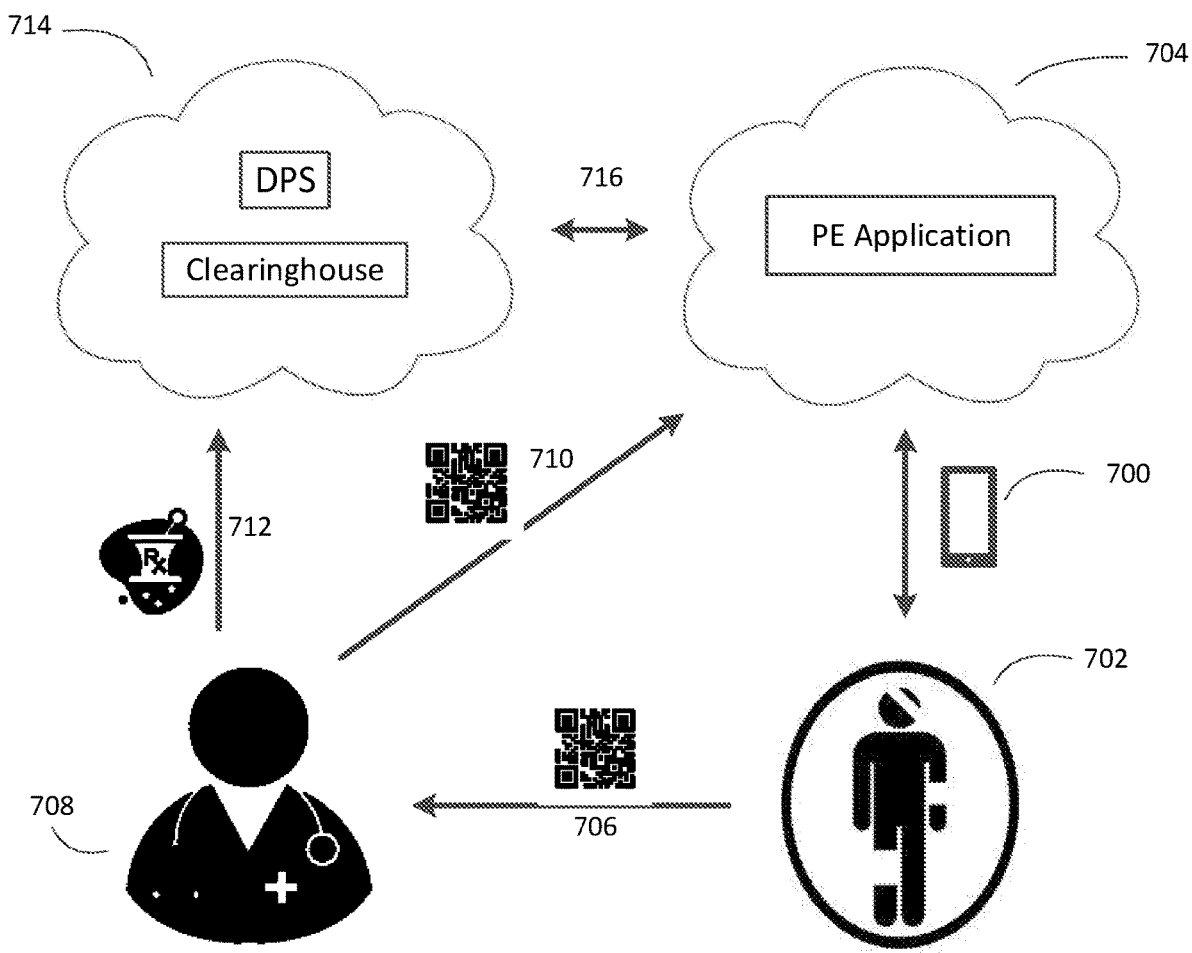
FIG. 7 is a view of prescribing practice consistent with certain embodiments of the present invention.

Turning now to FIG. 7, a view of prescribing practice consistent with certain embodiments of the present invention is shown. Patient 702 registers with the PE Application in Cloud Two 704 by using the CA 700. At 706 Patient 702 provides a CA-generated Machine-readable code key to Physician 708. At 710 Physician 708 communicates the patient-provided Machine-readable code key to the Physician's account in the PE Application in Cloud Two 704. At 712 Physician 708 communicates prescription details to the DPS and Clearinghouse in Cloud One 714. At 716 DPS and Clearinghouse in Cloud One 714 communicates with the PE Application in Cloud Two 704.

Figure 8:
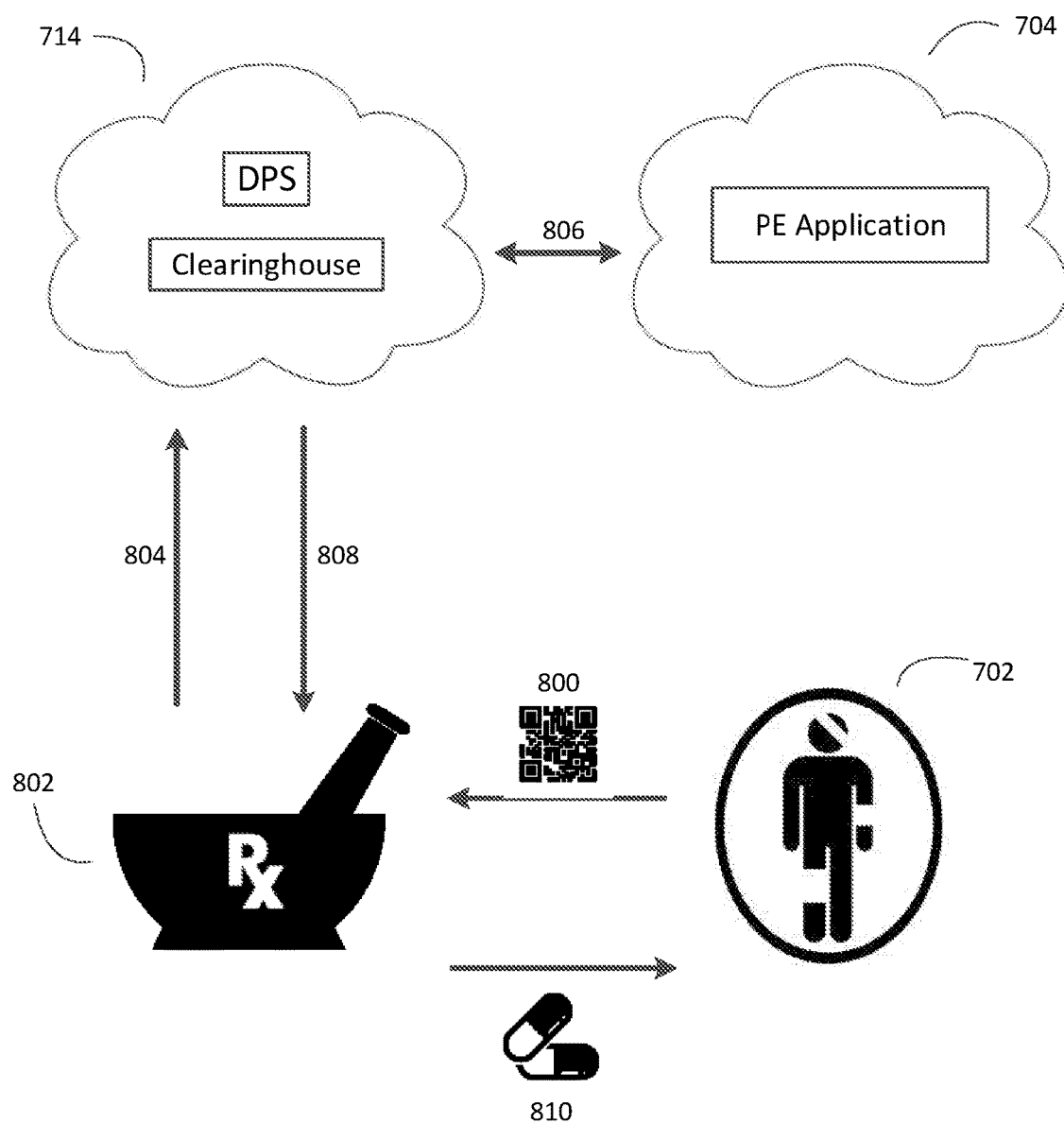
FIG. 8 is a view of prescription fulfillment consistent with certain embodiments of the present invention.

Turning now to FIG. 8, a view of prescription fulfillment consistent with certain embodiments of the present invention is shown. Patient 702 at 800 presents the CA-generated Machine-readable code key to Pharmacist 802. At 804, Pharmacist 802 communicates with the DPS and Clearinghouse in Cloud One 714, seeking verification of the prescription. At 806 the DPS and Clearinghouse in Cloud One 714 communicates with the PE Application in Could Two 704, thereby confirming the presence of a valid prescription. At 808 the DPS and Clearinghouse in Cloud One 714 sends a prescription verification confirmation message to the Pharmacist 802. At 810 the Pharmacist 802 provides a filled prescription to Patient 702.

While certain illustrative embodiments have been described, it is evident that many alternatives, modifications, permutations and variations will become apparent to those skilled in the art in light of the foregoing description.

I claim:

1. A method for requesting and receiving prescription verification, comprising:

initializing a secure communication channel between a mobile device and a server connected to a pharmacy, the server initializing a secure communications channel between the server and a separate electronic clearinghouse comprising a secure database of prescription information;

generating a patient identification code key containing encrypted patient information unique to a particular patient;

a client application registered to a patient generating a time-sensitive unique encrypted machine-readable code key for said patient that is tied to and referencing a particular prescription and containing a pre-configured expiration time span for said code key;

said time sensitive unique encrypted machine-readable code key having an authorized time span that is dynamically configured as a particular time-offset time span as a time-offset from an exterior event where the exterior event is the creation of said time sensitive unique encrypted machine-readable code key;

the physician transmitting prescription information to said separate electronic clearinghouse;

a patient submitting the patient identification code key and said time sensitive unique encrypted machine-readable code key to said pharmacy for fulfillment;

the pharmacy seeking prescription verification from the clearinghouse of stored prescription parameters of medication and dosage to provide for a verification against pharmacy inventory;

the clearinghouse transmitting the prescription parameters and returning verification of said parameters to the pharmacy;

the pharmacy operative to fulfill the verified prescription utilizing said patient identification code key and said verification of the prescription parameters prior to the expiration of said time sensitive prescription authorized time span;

where the secure communications channel is initiated from a mobile application downloaded to the mobile device; and each communication to and from said mobile device is secured through a unique encryption key and decipher key that is unique to a user for whom it is generated and with whom said unique encryption key and decipher key is associated.

2. The method of claim 1, where both the server and the clearinghouse are cloud-based.

3. The method of claim 2, where the server and the clearinghouse are based in different clouds.

4. The method of claim 1, where the machine-readable code is a QR-Code.

5. A system for requesting and receiving prescription verification, comprising:

a server connected to a pharmacy in secure communication with a mobile device;

the server initializing a secure communications channel between the server and a separate electronic clearinghouse comprising a secure database of prescription information;

a patient smart device generating a patient identification code key containing encrypted patient information unique to a particular patient;

a physician transmitting the patient identification code key to the server;

a client application registered to a patient generating a time-sensitive unique encrypted machine-readable code key for said patient that is tied to and referencing a particular prescription and containing a pre-configured expiration time span for said code key;

said time sensitive unique encrypted machine-readable code key having an authorized time span that is dynamically configured as a particular time-offset time span as a time-offset from an exterior event where the exterior event is the creation of said time sensitive unique encrypted machine-readable code key;

a patient submitting the patient identification code key and said time sensitive unique encrypted machine-readable code key to said pharmacy for fulfillment;

the pharmacy seeking prescription verification from the clearinghouse of the stored prescription parameters of medication and dosage, to provide for a verification against pharmacy inventory;

the clearinghouse transmitting the prescription parameters and returning verification of said parameters to the pharmacy; and the pharmacy operative to fulfill the verified prescription utilizing said patient identification code key and said verification of the prescription parameters prior to the expiration of said time sensitive prescription authorized time span;

where the secure communications channel is initiated from a mobile application downloaded to the mobile device; and each communication to and from said mobile device is secured through a unique encryption key and decipher key that is unique to a user for whom it is generated and with whom said unique encryption key and decipher key is associated.

6. The system of claim 5, where both the server and the clearinghouse are cloud-based.

7. The system of claim 6, where the server and the clearinghouse are based in different clouds.

8. The system of claim 5, where the machine-readable code is a QR-Code.

* * * * *